(12) United States Patent
Basri et al.

(10) Patent No.: US 8,598,236 B2
(45) Date of Patent: Dec. 3, 2013

(54) EMULSION SYSTEM DERIVED FROM ENGKABANG FAT ESTERS

(75) Inventors: Mahiran Basri, Serdang (MY); Siti Salwa Abd Gani, Serdang (MY); Nur Fariza Abd Rahman, Serdang (MY); Abu Bakar Salleh, Serdang (MY); Mohm Basyaruddin Abd Rahman, Serdang (MY); Raja Noor Zaliha Raja Abdul, Serdang (MY)

(73) Assignee: Universiti Putra Malaysia, Selangor (MY)

( * ) Notice: Subject to any disclaimer, the term of this patent is extended or adjusted under 35 U.S.C. 154(b) by 0 days.

(21) Appl. No.: 13/380,620

(22) PCT Filed: Jun. 22, 2010

(86) PCT No.: PCT/MY2010/000106
§ 371 (c)(1),
(2), (4) Date: Mar. 5, 2012

(87) PCT Pub. No.: WO2010/151104
PCT Pub. Date: Dec. 29, 2010

(65) Prior Publication Data
US 2012/0165415 A1 Jun. 28, 2012

(30) Foreign Application Priority Data

Jun. 23, 2009 (MY) .................... 20092650

(51) Int. Cl.
*A61K 47/44* (2006.01)
*A61K 8/92* (2006.01)

(52) U.S. Cl.
USPC .................... 514/785; 424/400

(58) Field of Classification Search
None
See application file for complete search history.

(56) References Cited

U.S. PATENT DOCUMENTS 6,267,985 B1 * 7/2001 Chen et al. ............ 424/451

FOREIGN PATENT DOCUMENTS

FR 2700954 8/1994

OTHER PUBLICATIONS

Chemie Alliance Official Website—Chemie Alliance's Products (retrieved from Internet on Dec. 23, 2011), URL: http://www.alliance2u.cem/preducts_chmI.asp?cat=ADD, admitted as prior art in IDS.*
Chemie Alliance Official Website—Chemie Alliance's Products (retrieved from Internet on Dec. 23, 2011), URL: http://www.alliance2u.com/products_chm1.asp?cat=ADD.
Djekic, L. and Primorac, M., (2008), "The influence of cosurfactants and oils on the formation of pharmaceutical microemulsions based on PEG-8 caprylic/capric glycerides," International Journal of Pharmaceutics, vol. 352, pp. 231-239.
English Abstract of FR 2700954.

* cited by examiner

*Primary Examiner* — Ernst Arnold
*Assistant Examiner* — Jianfeng Song
(74) *Attorney, Agent, or Firm* — Preston Smirman; Smirman IP Law, PLLC

(57) ABSTRACT

An isotropic or homogeneous emulsion system comprises an oil phase including fat esters of illipe fat and a solubilizer; a non-ionic surfactants; and deionized water; characterized in that the solubilizer is a mixture of polyethyleneglycol-40 hydrogenated castor oil, polysorbate 20 and octoxynol-12.

26 Claims, 9 Drawing Sheets

Before Purification Process

After Purification Process

EMULSION SYSTEM DERIVED FROM ENGKABANG FAT ESTERS

CROSS-REFERENCE TO RELATED APPLICATION

The instant application is a national phase of, and claims priority to, PCT International Application No. PCT/MY2010/000106, filed on Jun. 22, 2010, pending, and Malaysian Patent Application No. PI 20092650, filed Jun. 23, 2009, pending, the entire specifications of both of which are expressly incorporated herein by reference.

FIELD OF THE INVENTION

The present invention relates to an isotropic or homogeneous emulsions system which can be used for preparing cosmetic or pharmaceutical products. In more specific, the present invention employs fat esters derived from illipe fat as the oil phase of the emulsion system while other ingredient such as solubilizers and surfactant are used in conjunction at a specific ratio in the present invention to create an isotropic and homogenous milky emulsions system.

BACKGROUND OF THE INVENTION

Wax esters or fat esters have a wide range of applications as lubricants, polishes, plasticizers, antifoaming agents, coating materials in different industries. Particularly in cosmetics, wax esters are formulated with other ingredient in the delivery system, preferably in an emulsion form, to cater aesthetic effect to the user upon applying the formulated emulsion. Emulsions are mixtures of two insoluble materials containing water and oil phase which are stabilized against separation using emulsifier (surfactant). Emulsions are defined as heterogeneous systems in which at least one immiscible or barely miscible liquid is disperse in another liquid in the faun of tiny droplets of various sizes.

In an emulsion while on storage, several breakdown processes may occur such as creaming, sedimentation and flocculation. To avoid or slow the breakdown process, the emulsion formed is preferably in the isotropic state. Thus, choosing the right emulsifier or other stabilizing agent is crucial. Study of emulsion stability in systems with comparable amounts of oil and water, with low nonionic surfactant content have shown the strong correlation between the phase inversion phenomenon and the existence of three isotropic phase equilibria with low or ultra low interfacial tensions. The surfactant phase is then the very microemulsion domain, which is the stable state of these oil/water mixtures in the presence of a small surfactant amount. An accurate determination of the hydrophilic-lipophilic nature of surfactants plays an essential role in guiding the formulation of microemulsion. Nonetheless, fat esters of various source contains carbon chains of different length which, possibly, only react with certain type of emulsifier or stabilizing agent to achieve the isotropic state.

Emulsions containing illipe-based fat esters have their own specialty. Illipe is the name of tree that comes from the genus of 'shorea'. Illipe fat can be obtained from the seed and it is also known as illipe butter. Illipe butter is classified as exotic butter that can moisturizes the skin and restores elasticity. It also can prevent dry skin, the development of wrinkles and reduce degeneration of skin cells. Illipe fat esters were produces by reaction oleyl alcohol and illipe fat. Thus far, no work is being devoted to develop an isotropic and homogenous milky emulsions system based on illipe fat esters.

SUMMARY OF THE INVENTION

The present invention aims to provide an emulsion system to be used in the preparation of cosmetic and/or pharmaceutical products. Specifically, the emulsion system contains an oil phase having fat esters of illipe fat and one or more surfactants in a specified ratio to effectively deliver the active agent of the cosmetic and/or pharmaceutical products to the site of action in the user's body.

The present invention also provides an isotropic or homogenous milky emulsions system which the pharmaceutical and/or cosmetic products derived thereof have good resistance against degradation thus enhance shelf-life of the derived products.

At least one of the preceding objects is met, in whole or in part, by the present invention, in which one of the embodiment of the present invention includes an isotropic and homogenous milky emulsions system comprising an oil phase including fat esters of illipe fat and a solubilizer; a non-ionic surfactants; and deionized water; characterized in that the solubilizer is a mixture of polyethyleneglycol-40 hydrogenated castor oil, polysorbate 20 and octoxynol-12.

In order to form an isotropic emulsion system, the fat esters derived from illipe fat and the solubilizer in the present invention are in a ratio of 4 to 2:2 to 1 by weight percentage. Moreover, the oil phase and the non-ionic surfactant are in a ratio of 3 to 5:3 to 7 by weight percentage, while the oil phase and deionized water are in a ratio of 3 to 5:1 to 4 by weight percentage.

Further in the embodiment where homogenous emulsion system is prepared, the solubilizers are in a ratio similar to the isotropic emulsion system which is 4 to 2:2 to 1 by weight percentage. Following to this embodiment, the oil phase and the non-ionic surfactant are in a ratio of 1 to 5:2 to 5 by weight percentage, while the oil phase and deionized water are in a ratio of 1 to 5:4 to 7 by weight percentage.

In another aspect, the fat esters of illipe fat are acquired through alcoholysis of illipe fat by a long chain alcohol in a ratio of 1:1 to 4 in the presence of lipase in an organic solvent. Preferably, the organic solvent has a log P value more than 3.5.

DETAILED DESCRIPTION OF THE INVENTION

It is to be understood that the present invention may be embodied in other specific forms and is not limited to the sole embodiment described herein. However modification and equivalents of the disclosed concepts such as those which readily occur to one skilled in the art are intended to be included within the scope of the claims which are appended thereto.

The present invention is an isotropic emulsion or homogenous system comprising an oil phase including fat esters of illipe fat and a solubilizer; a non-ionic surfactants; and deionized water; characterized in that the solubilizer is a mixture of polyethyleneglycol-40 hydrogenated castor oil, polysorbate 20 and octoxynol-12. It is important to be noted that an isotropic and homogenous milky emulsions system crucially affect the shelf-life and effectiveness as a delivery vehicle in preparing a cosmetic and/or pharmaceutical product. An isotropic and homogenous milky emulsions system possesses good resistance towards degradation of the prepared products possibly caused by creaming, sedimentation, flocculation, phase inversion, coalescence of an ineffective emulsion system used. Though homogeneous emulsion shows lesser advantages possessed by the isotropic emulsion in terms of good resistance towards degradation, the homogeneous emulsion still can function as a good vehicle to effectively deliver active agent or drugs in a pharmaceutical composition derived thereon. Therefore, embodiments of the present invention include also homogeneous emulsion system. Isotropic emulsion is a transparent/translucent through the naked eye and the particle size is below than 100 nm. Homogenous emulsion is white or milky in color and the particle size is more than 100 nm. Both of them could be used in the formulation of cosmetics and pharmaceutical products depend on their applications.

In the preferred embodiment, the fat esters derived from illipe fat and the solubilizer is in a ratio of 4 to 2:2 to 1 by weight percentage. Utilization of the solubilizer in the present invention allows the oil phase, the water phase and the surfactant to react in a much wider range for obtaining an isotropic and homogenous milky emulsion system as shown in the ternary phase diagram in FIG. 7. This feature permits the disclosed emulsion system to be prepared to suit and optimally deliver active agent of a cosmetic and/or a pharmaceutical product though mixing the different elements within their respective wide range. Moreover, the solubilizer used in the more preferred embodiment can be obtained in a commercially available product with a tradename of SOLUBILISANT GAMMA 2429. Nonetheless, solubilizer of the same category such as SOLUBILISANT GAMMA 2421 containing mostly mixture of Octoxynol-12 and polysorbate 20 maybe useable in the present invention too.

It was found by the inventor of the present invention, the oil phase and the non-ionic surfactant is preferably prepared in a ratio of 3 to 5:3 to 7 by weight percentage in order to form an isotropic emulsion system. The micelle in the emulsion system is found to be stable for a long duration at this ratio thus attaining the stated object and advantages of the present invention. For the case of homogeneous emulsion system, the oil phase and the non-ionic surfactant are in a ratio of 1 to 5:2 to 5 by weight percentage. The nonionic surfactant can be alkyl polyethyleneoxide and/or derivatives, alkylphenol polyethylene oxide and/or derivatives, Copolymers of poly (ethylene oxide) and polypropylene oxide), fatty alcohol and/or derivatives, coamide MEA and/or derivatives, coamide DEA and/or derivatives, polysorbates and/or derivatives. It is more preferred that the non-ionic surfactant is commercially available non-ionic surfactant such as Span 80, Span 20, Tween 85 or Tween 80, while the most preferred embodiment employs Tween 85. Similarly, the oil phase and deionized water is in a ratio of 3 to 5:1 to 4 by weight percentage to form the isotropic emulsion system, while the oil phase and deionized water are in a ratio of 1 to 5:4 to 7 by weight percentage to acquire the homogeneous emulsion system.

According to the preferred embodiment the fat esters of illipe fat is acquired through alcoholysis of illipe fat by a long chain alcohol (fatty alcohol) in a ratio of 1:1 to 4 in the presence of lipase in an organic solvent that the alcohol preferably has a carbon chain of 12 to 18 carbon atoms per molecule. Oleyl alcohol was used in this reaction.

The other name for oleyl alcohol is octadecenol or cis-9-octadecen-1-ol and the chemical formula is $C_{18}H_{36}O$. The reaction is preferably conducted at 30° C. to 60° C., or more preferable at 50° C. with or without physical stirring. Variation of the reaction temperature can significantly affect the substrate solubility thus the reaction rate, enzyme stability and reactivity of the reaction. In further embodiment, the organic solvent to be used in the illipe fat esters preparation has a log P value more than 3.5 to dissolve the reaction ingredients. Furthermore, the lipase is acquired from *Rhizomucor miehei* (Lipozyme RM IM). More preferable, the lipase of the present invention is immobilized on a support thus the reaction can be terminated by removing the enzyme from the ingredient mixture and the lipase can be recycled as well for reuse upon sufficient cleaning.

The following example is intended to further illustrate the invention, without any intent for the invention to be limited to the specific embodiments described therein.

Example 1

Engkabang fat was obtained from Sarawak, Malaysia. Fatty acid compositions of engkabang fat are 43.7% of stearic acid, 35.7% of oleic acid, 19.9% of palmitic acid, 0.4% of linolic acid and 0.1% of palmitoloc acid [10]. Sorbitan monooleate (Span80), sorbitan monolaurate (Span20), polyoxyethylene (20) sorbitan tri-oleate (Tween85) and polyoxythylene (20) sorbitan mono-oleate (Tween80) were purchased from Merck Schuchardt OHG, Hohenbrunn, Germany. The HLB values of Span80, Span20, Tween85 and Tween80 are 4.3, 8.6, 11.0 and 15.0, respectively. Oleyl alcohol (cis-9-Octadecen-1-ol) and n-heptane were also purchased from Merck Schuchardt OHG, Hohenbrunn, Germany. Lipozyme® RM IM was purchased from Novozymes A/S-Krogshoejvej 36-2880 Bagsvaerd, Denmark. Solubilisant Gamma 2429 was purchased from Gattefosse, USA. Deionized water was produced in our laboratory.

Engkabang fat esters were synthesized through alcoholysis reaction using enzymatic method. For an alcoholysis reaction, 10 mmol engkabang fat and 30 mmol oleyl alcohol were mixed (in molar ratio 1:3). Then, 1.5 g Lipozyme was placed into a reaction bottle and n-heptane was added until a total volume of 100 mL was attained.

The reaction bottle was tightly closed. The reaction mixture was incubated in a horizontal water bath shaker with a speed 150 rpm for 5 hours at 40° C. After the reaction was completed, the mixture was then filtered to separate the sample and the enzyme. The sample was subjected to rotary vacuum evaporator at 98° C. to remove n-heptane. Finally, the crude engkabang fat esters was put in a separation funnel. Ethanol was added with a ratio of engkabang fat esters:ethanol, 1:3. The separation funnel was shaken and left to settle. Two layers appeared whereby engkabang fat esters were at the bottom of the separation funnel and the ethanol containing oleyl alcohol was at the top. This step was repeated three times. Then, the sample of engkabang fat ester was collected from the separation funnel. The ethanol was recovered using rotary vacuum evaporator at ±78° C.

Example 2

Samples of engkabang fat, oleyl alcohol and engkabang fat esters were separated on silica gel plates (Merck, DC-aluminium folein Kiesel, gel 60 $F_{254}$). The eluent, leading to the best achievable separation of the different components, consisted of a mixture of n-heptane/diethyl ether (80:20, v/v). After the elution, the plates were dried and stored in iodine chamber. The presence of the oleyl alcohol, engkabang fat and engkabang fat esters were detected as brown spots.

Figure 1:
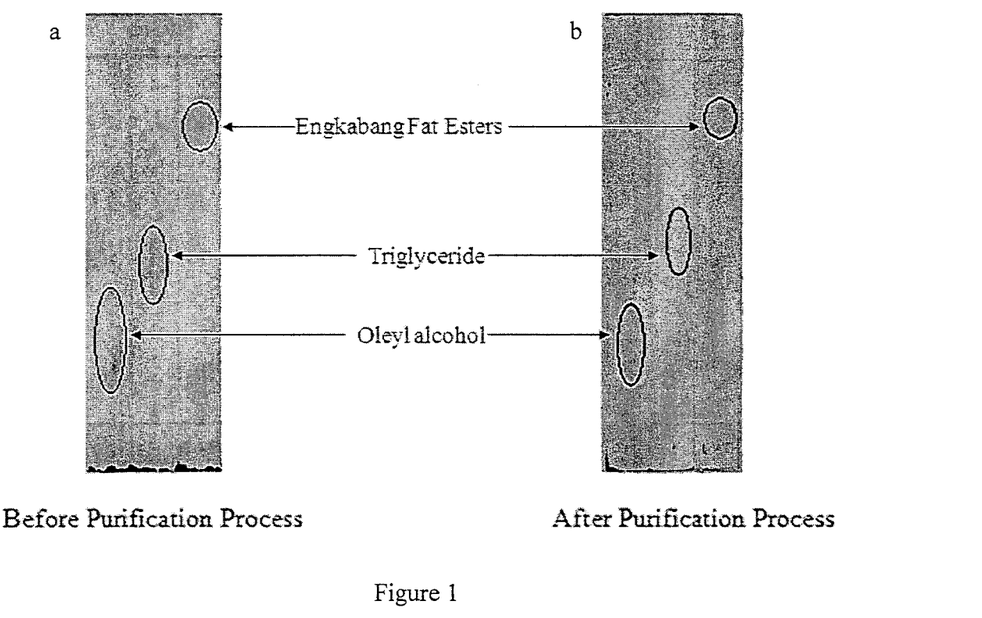
FIG. 1 is a thin layer chromatography of engkabang fat, oleyl alcohol and engkabang fat esters (a) before purification process and (b) after purification process.

FIG. 1 depicts the TLC analysis of engkabang fat esters. Lane 1 represented oleyl alcohol with $R_f$ value 0.11 whilst engkabang fat was shown at lane 2 with $R_f$ value of the triglyceride at 0.35. There were trace amount of diglycerides and monoglycerides found in the mixture with the $R_f$ value 0.05 and 0.01 respectively. The formation of new product was shown in lane 3 which was the spot of engkabang fat esters. The first TLC plate was the chromatogram of engkabang fat esters before purification and the second was the chromatogram of engkabang fat esters after purification. Oleyl alcohol with the higher polarity has been absorbed to the stationary phase more than triglycerides in engkabang fat. The spot of engkabang fat esters appeared on the top of TLC plate with the $R_f$ value 0.76 as engkabang fat esters were the least polar as compared to triglyceride and oleyl alcohol. The more polar compound has difficulty to go up on the TLC plate as the silica gel on the TLC plate is more attracted to the polar compound. The lane for engkabang fat esters before purification contained three clear spots. The two spots appeared at the $R_f$ value 0.01 and 0.05 were the unreacted engkabang fat and oleyl alcohol respectively. Only a single spot of fat esters were observed at lane 3 after the sample was purified.

Example 3

GC analysis was conducted by injecting 0.5 µl aliquot into a Shimadzu GC-9A gas chromatography in a split mode equipped with a flame-ionization detector and a RTX65 capillary column (30 m×0.25 mm i.d.; film thickness 0.25 µm; Restex Corporation, USA). Injector and detector temperature were set at 300 and 320° C., respectively. Oven temperature was maintained at 180° C. for 2 minutes, increased to 300° C. with the ramping time 20° C./min and held for 10 minutes. Nitrogen was used as the carrier gas with the flow rate 50 ml/min. The product composition was quantitated by an internal standard method with methyl arachidate as the internal standard.

Figure 2:
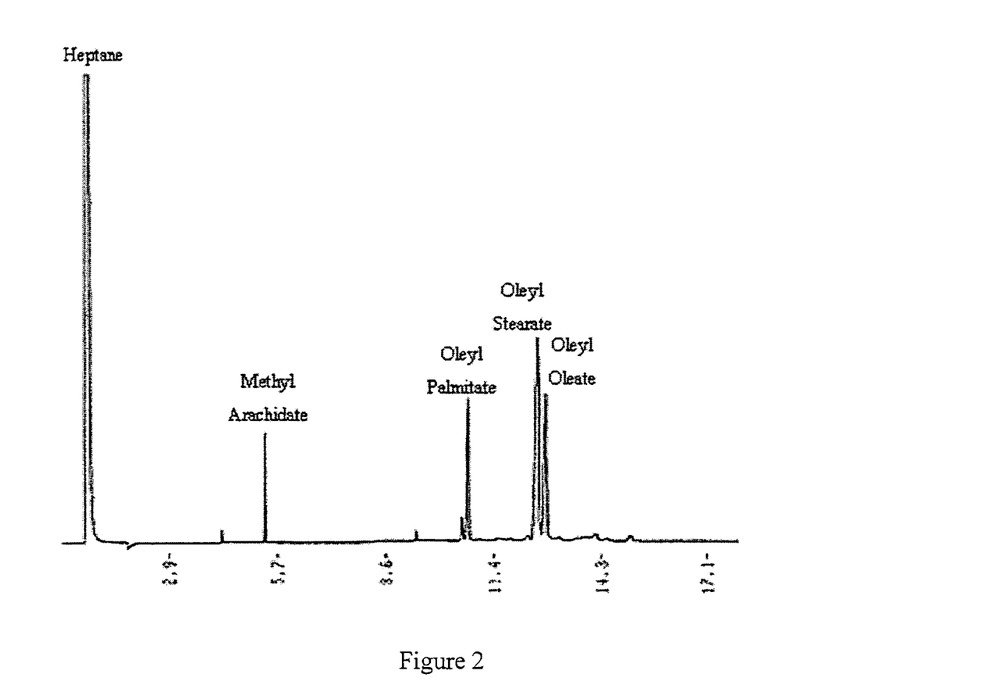
FIG. 2 shows the chromatogram of the fat esters sample derived from the alcoholysis process using lipase as biocatalyst.

FIG. 2 depicts the chromatogram of engkabang fat esters synthesized using Lipozyme. Five major peaks appeared in the chromatogram. The first peak was n-heptane as solvent, the second peak was methyl arachidate as the internal standard. The other three peaks were fatty acid esters namely oleyl palmitate, oleyl stearate and oleyl oleate. They were identified at $t_R$ 10.28, 12.06 and 12.27 min respectively. Oleyl alcohol reacted with triglyceride in the engkabang fat to produce engkabang fat esters. The percentage yield of oleyl palmitate, oleyl stearate and oleyl oleate produced were 17.51%, 40.84% and 35.32% respectively. The total percentage yield of engkabang fat esters synthesized was 93.67%.

Example 4

Engkabang fat esters/nonionic surfactant:deionized water were weighed at various weights ranging from 0:100 to 100:0 (w/w). The mixture with a total weight of 0.5 g was placed in a 10 ml screw-cap glass tube. The samples were then centrifuged for 15 minutes at 4000 rpm. The phase behaviors of the samples were examined through polarized light microscope, Nikon Eclipse 80i, Japan. The experiment was repeated with the addition of deionized water according to its percentage from 0% to 100%.

The phase behaviors were observed and shown in the ternary phase diagrams. Five ternary phase diagrams were constructed using four nonionic surfactants. Comparisons among the ternary phase diagrams were made to see the changes when the different HLB values of the nonionic surfactants were used.

Figure 3:
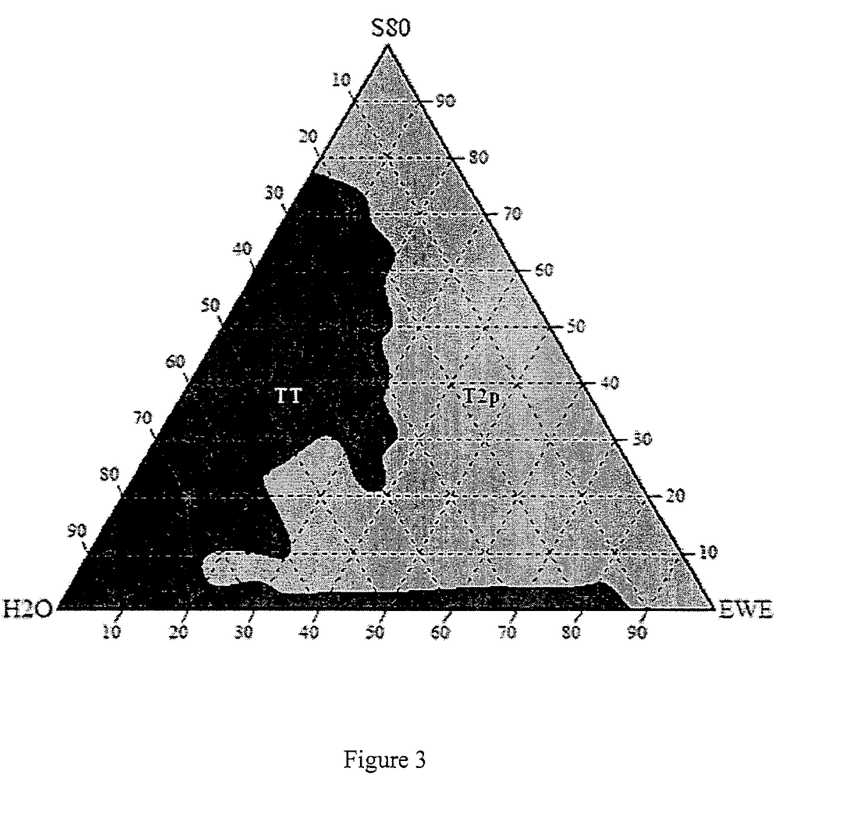
FIG. 3 is a ternary phase diagram of the emulsion system prepared from illipe fat esters (EWE), Span 80 and dionized water which T2p refers to two-phase region and TT refers to three phase region.

FIG. 3 depicts the ternary phase diagram of engkabang fat esters/Span80/deionized water. Two regions appeared in this ternary phase diagram, two-phase and three-phase regions. It was observed that the two-phase region was formed along the apex line of Span80 and engkabang fat esters. The two-phase region appeared at the right of ternary phase diagram where the percentages of deionized water were low. The three-phase region appeared on the left of ternary phase diagram where the percentages of deionized water were high. Even as the structure of engkabang fat esters were simpler as compared with the structure of engkabang fat, Span80 still could not be combined with the engkabang fat esters to give homogenous or isotropic region.

Figure 4:
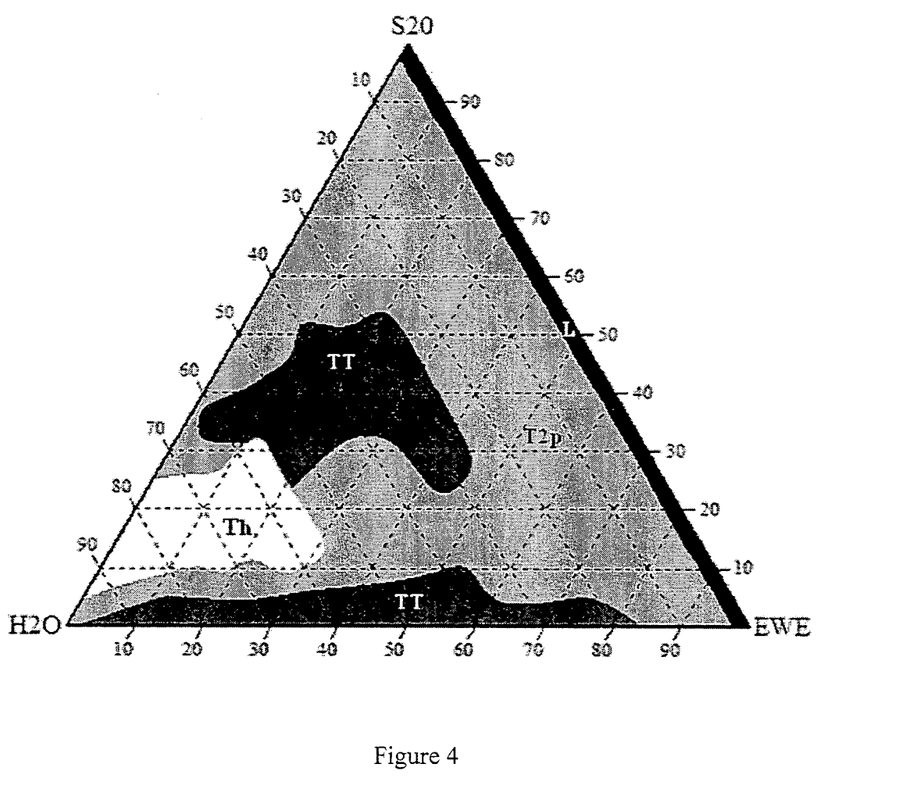
FIG. 4 is a ternary phase diagram of the emulsion system prepared from illipe fat esters (EWE), Span 20 and deionized water which T2p refers to two-phase region, TT refers to three phase region, L refers to isotropic region and Th refers to homogenous milky region.

FIG. 4 depicts the ternary phase diagram of engkabang fat esters/Span20/deionized water. The isotropic region appeared along the apex line of Span20 and engkabang fat esters. The homogenous region was found at the water-rich corner in the system which is classified as o/w emulsions. The two-phase region was the largest region observed in this ternary phase diagram. The three-phase region appeared at the percentages of deionized water around 16% to 100% at the low percentage region of Span20. The three-phase region also appeared at the middle of ternary phase diagram.

Figure 5:
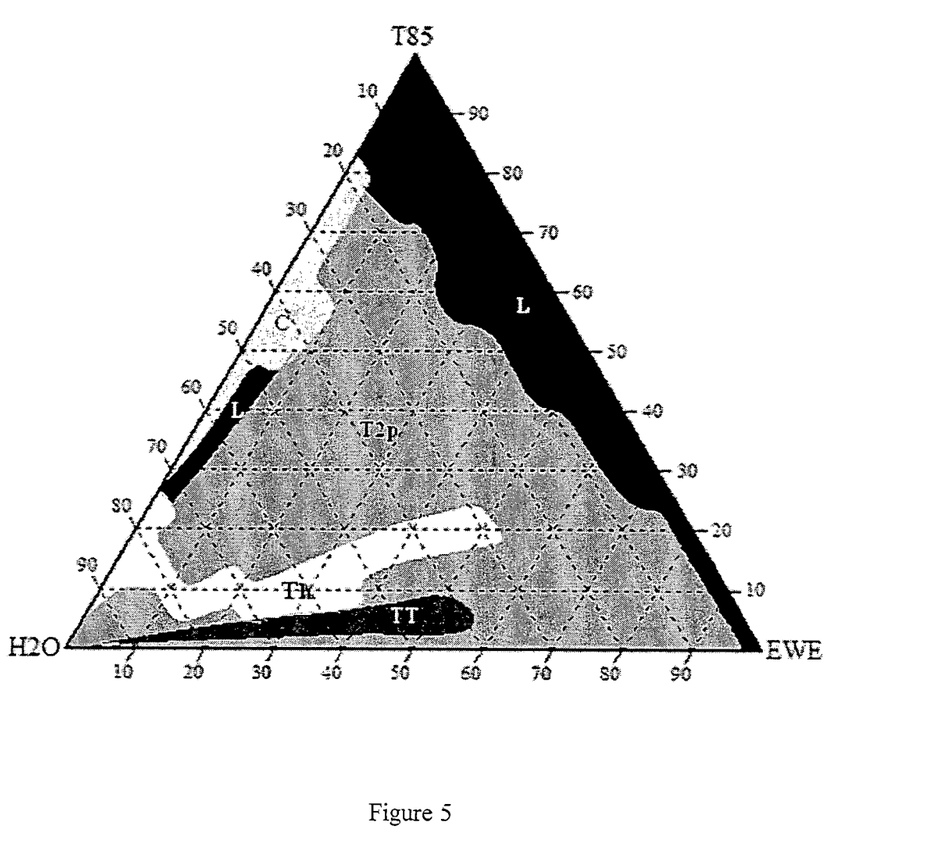
FIG. 5 is a ternary phase diagram of the emulsion system prepared from illipe fat esters (EWE), Tween 85 and deionized water which T2p refers to two-phase region, TT refers to three phase region, L refers to isotropic region and Th refers to homogenous milky region.

FIG. 5 depicts the ternary phase diagram of engkabang fat esters/Tween85/deionized water. The liquid crystal region appeared at the low percentage of engkabang fat esters where the percentage of deionized water around 20% to 70%. It also appeared at around 40% to 50% of deionized water. It was observed that the isotropic region was formed along the apex line of Tween85 and engkabang fat esters. The homogenous region was found at the water-rich corner in the system. Most of the two-phase region appeared at the middle of the system. The three phase region started to appear at the low percentage of Tween85 where the percentage of deionized water was around 40% and above.

Figure 6:
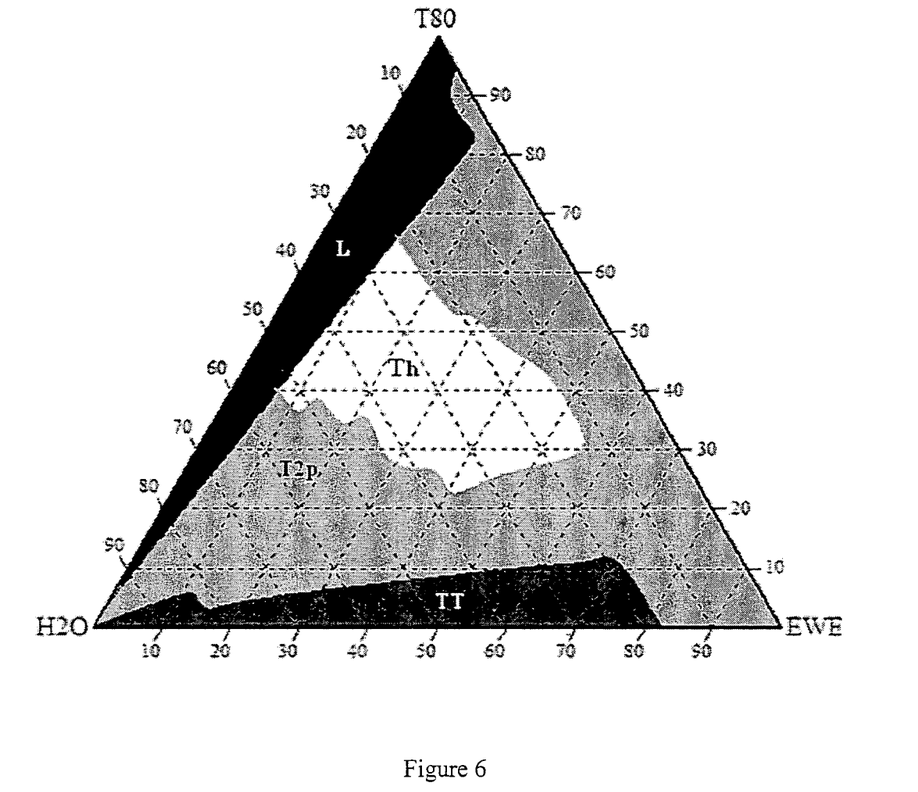
FIG. 6 is a ternary phase diagram of the emulsion system prepared from illipe fat esters (EWE), Tween 80 and deionized water which T2p refers to two-phase region, TT refers to three phase region, L refers to isotropic region and Th refers to homogenous milky region.

FIG. 6 depicts the ternary phase diagram of engkabang fat esters/Tween80/deionized water. The isotropic region was found along the apex line of Tween80 and deionized water at the low percentage of engkabang fat esters. The homogenous milky region appeared at the middle of ternary phase diagram where the percentage of deionized water was around 20% to 50%. The two phase region was the largest region appeared in that ternary phase diagram. The three-phase region appeared at the low percentage of Tween80.

Figure 7:
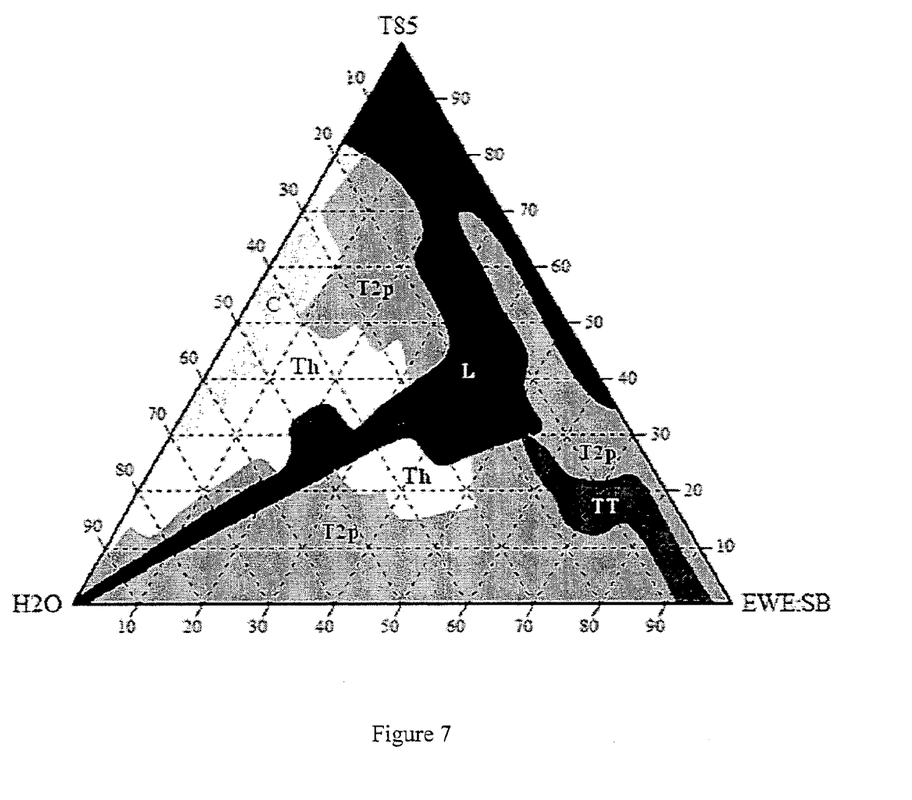
FIG. 7 is a ternary phase diagram of the emulsion system prepared from illipe fat esters (EWE) with solubilisant gamma, Tween 85 and deionized water which T2p refers to two-phase region, TT refers to three phase region, L refers to isotropic region and Th refers to homogenous milky region.

FIG. 7 depicts the ternary phase diagram of engkabang fat esters:solubilisant gamma/Tween85/deionized water. The ratio of engkabang fat ester:solubilisant gamma was 2:1. In this ternary phase diagram, liquid crystal, isotropic and homogenous milky regions were larger as compared to those in the ternary phase diagram of engkabang fat esters/Tween85/deionized water. The three-phase region appeared at low percentages of deionized water and Tween85, but the region was quite small. The combination of engkabang fat esters:solubilisant gamma/Tween85/deionized water produced larger liquid crystal, isotropic and homogenous milky regions as compared to the other ternary phase diagrams.

Example 5

A batchwise operation was carried out on a laboratory scale in a 500 ml stirred batch reactor with one multi bladed Rushton turbine impeller as an agitator. Engkabang fat (1.0 mmol) and oleyl alcohol (2.5 mmol) were weighed and placed into the reactor followed by the addition of n-heptane to a total volume of 375 mL as solvent. Then, lipase (5.50 g) was added subsequently to the reaction mixture and was reacted at temperature of 45° C. The reaction was performed with agitation speed of 250 rpm continuously for 5 hours.

The reaction was terminated by separating the enzyme from the mixture via filtration using the sieves. The reaction mixture (25 µL) was pipetted and diluted with 1 mL of n-heptane in a vial. Internal standard was incorporated into mixture in the vial before being subjected to gas chromatography (GC). The product composition is quantitated using an internal standard method which allows the calculation of percentage yield of fat esters produced. The product has a relative yield more than 90%.

Figure 8:
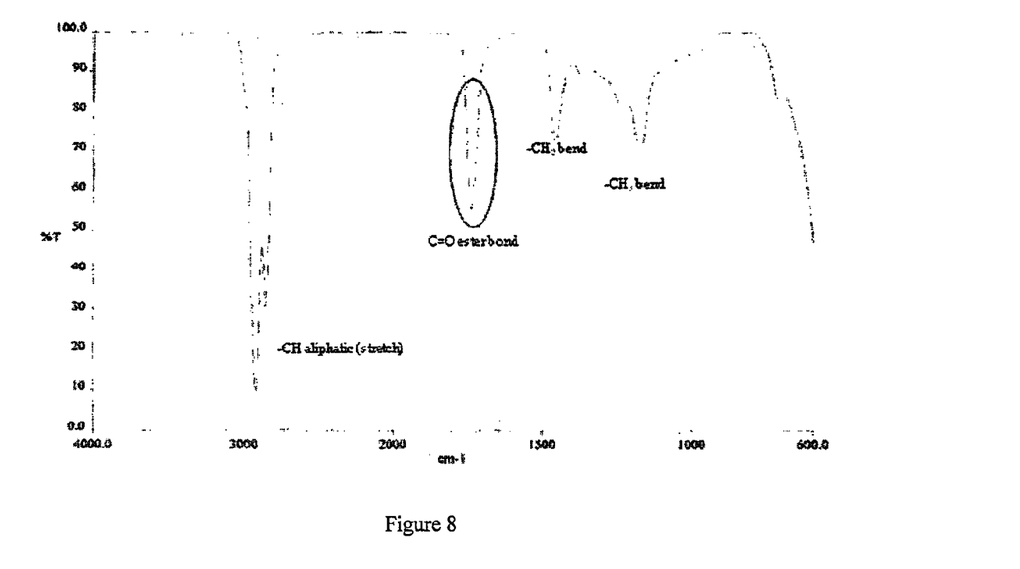
FIG. 8 is a FT-IR spectrum of the illipe fat esters showing the presence of C=O functional group for ester.
Figure 9:
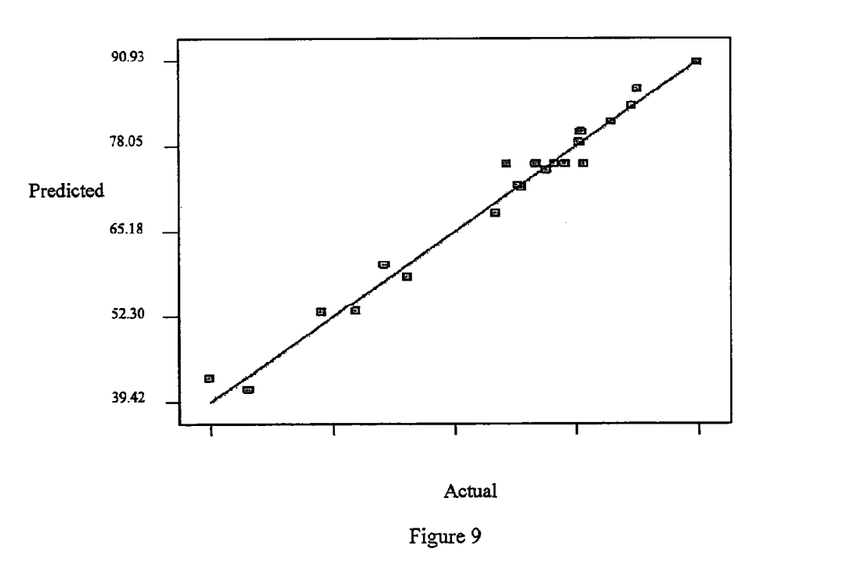
FIG. 9 is a graph showing RSM correlation between the actual and predicted illipe fat esters yield.

FIG. 8 depicts the FT-JR spectrum of illipe fat esters. A sharp peak was shown at 1736.00 cm$^{-1}$ representing the existence of (C=O) bond for ester. The high intensity for this peak strongly proved the presence of ester group in the compound. The presence of (C—O) bond in the compound was shown by a peak at 1171.00 cm-1. The peak for alkyl groups were shown at 1458.00 cm$^{-1}$ and 1360.00 cm$^{-1}$, and the peak for alkanes was shown at 2921.00 cm$^{-1}$.

Example 6

Figure 10:
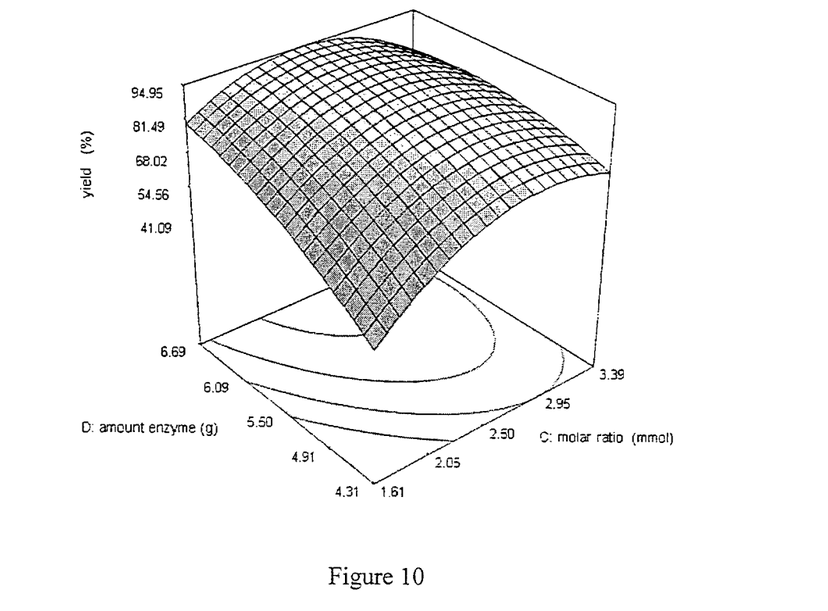
FIG. 10 is a response surface plot showing the effect of amount enzyme, substrate molar ratio and their interaction on the synthesis of illipe fat esters.

Example 5 was repeated by varying the amount of enzyme and substrate molar ratio at impeller speed of 250 rpm and temperature of 45° C. FIG. 10 depicts the response surface plots as a function of amount of enzyme, and substrate molar ratio interaction on the percentage yield of illipe fat esters. Reaction with increasing amount of enzyme and substrate molar ratio led to an increase of percentage yield. Maximal percentage yield (>90.00%) was obtained at molar ratio of 1:2.50-2.95 at highest amount of enzyme (6.69 g).

Example 7

Figure 11:
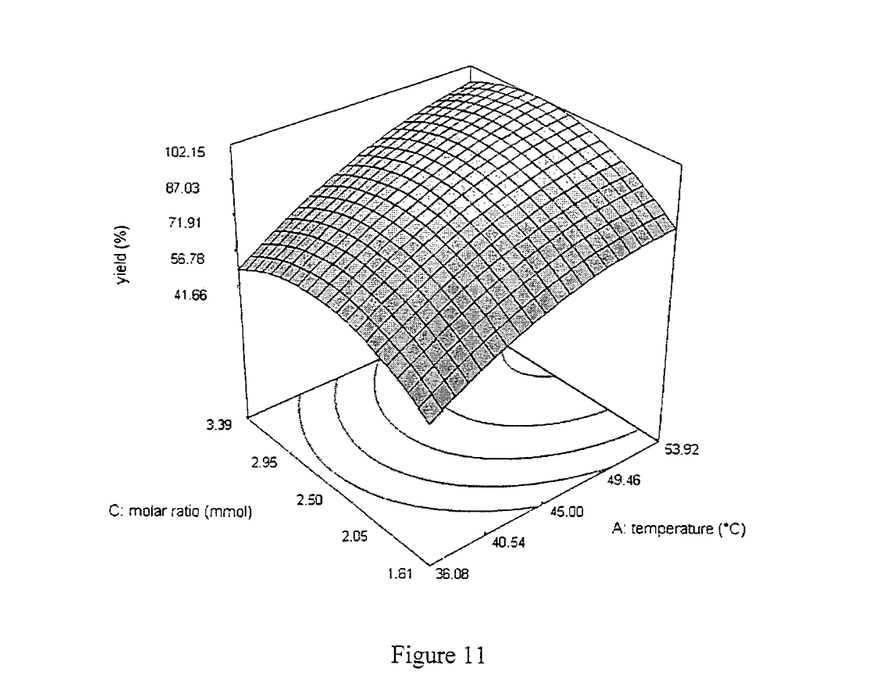
FIG. 11 is a response surface plot showing the effect of substrate molar ratio, temperature and their interaction on the synthesis of illipe fat esters.

Example 5 was repeated by varying the substrate molar ratio and temperature at 5.50 g amount of enzyme and impeller speed of 250 rpm. FIG. 11 depicts the response surface plots as a function of substrate molar ratio, and temperature interaction on the percentage yield of illipe fat esters. Reaction with increasing substrate molar ratio and temperature led to an increase of percentage yield. Maximal percentage yield (>90.00%) was obtained at molar ratio of 1:2.50-2.95 at temperature 53.92° C.

Example 8

Figure 12:
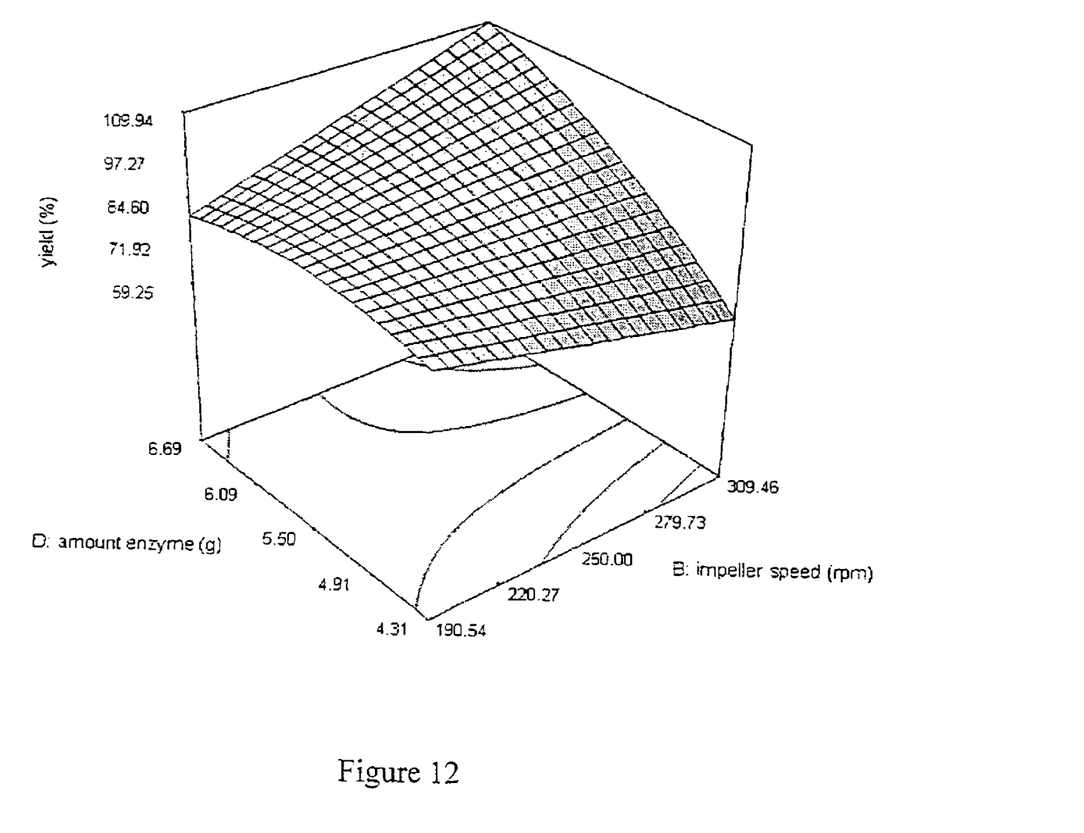
FIG. 12 is a response surface plot showing the effect of amount enzyme, impeller speed and their interaction on the synthesis of illipe fat esters.

Example 5 was repeated by varying the amount of enzyme and impeller speed at temperature 45° C. and molar ratio of 1:2.50 mmol. FIG. 12 depicts the response surface plots as a function of amount of enzyme, and impeller speed interaction on the percentage yield of illipe fat esters. Reaction with increasing amount of enzyme and impeller speed led to an increase of percentage yield. Maximal percentage yield (>90.00%) was obtained at amount of enzyme 6.69 g and impeller speed of 309.46 rpm.

Example 9

Fitting of the data to various models (linear, two factorial, quadratic and cubic) and their subsequent analysis of variance (optimization study) showed that production of Engkabang fat esters was most suitably described with quadratic polynomial model. The very small p-value (0.0001) and a suitable coefficient of determination, $R^2$=0.978, indicated the quadratic polynomial model was highly significant and sufficient to represent the actual relationship between the response and the significant variables.

Changes therein and other uses will occur to those skilled in the art which are encompassed within the scope of the invention as defined by the scope of the claims.

The invention claimed is:

1. A composition for preparing cosmetic or pharmaceutical products, comprising:
   a two or three phase isotropic or homogeneous milky emulsion system comprising:
   an oil phase including long chain alkyl esters of illipe fat and a solubilizer, wherein the long chain alkyl has a carbon chain of 12-18 carbon atoms per molecular;
   a non-ionic surfactant; and
   deionized water;
   wherein the solubilizer is a mixture of polyethyleneglycol-40 hydrogenated castor oil, polysorbate 20 and octoxynol-12.

2. The composition according to claim 1, wherein the long chain alkyl esters derived from illipe fat and the solubilizer are in a ratio of 4 to 2:2 to 1 by weight percentage.

3. The composition according to claim 1, wherein the oil phase and the non-ionic surfactant are in a ratio of 3 to 5:3 to 7 by weight percentage to acquire the isotropic emulsion system.

4. The composition according to claim 1, wherein the oil phase and deionized water are in a ratio of 3 to 5:1 to 4 by weight percentage to acquire the isotropic emulsion system.

5. The composition according to claim 1, wherein the oil phase and the non-ionic surfactant are in a ratio of 1 to 5:2 to 5 by weight percentage to acquire the homogeneous milky emulsion system.

6. The composition according to claim 1, wherein the oil phase and deionized water are in a ratio of 1 to 5:4 to 7 by weight percentage to acquire the homogeneous milky emulsion system.

7. The composition according to claim 1, wherein the non-ionic surfactant is sorbitan monooleate, sorbitan monolaurate, polyoxyethylene (20) sorbitan trioleate, or polyoxyethylene (20) sorbitan monooleate.

8. The composition according to claim 1, wherein the long chain alkyl esters of illipe fat are acquired through alcoholysis of illipe fat by a long chain alcohol in a ratio of 1:1 to 4 in the presence of lipase in an organic solvent, wherein the long chain alcohol has a carbon chain of 12 to 18 carbon atoms per molecule.

9. The composition according to claim 8, wherein the organic solvent has a log P value more than 3.5.

10. The composition according to claim 8, wherein the lipase is acquired from *Rhizomucor miehei*.

11. A composition for preparing cosmetic or pharmaceutical products, comprising:
a two or three phase homogeneous milky emulsion system comprising:
an oil phase including long chain alkyl esters of illipe fat and a solubilizer, wherein the long chain alkyl has a carbon chain of 12-18 carbon atoms per molecular;
a non-ionic surfactant; and
deionized water;
wherein the solubilizer is a mixture of polyethyleneglycol-40 hydrogenated castor oil, polysorbate 20 and octoxynol-12.

12. The composition according to claim 11, wherein the long chain alkyl esters derived from illipe fat and the solubilizer are in a ratio of 4 to 2:2 to 1 by weight percentage.

13. The composition according to claim 11, wherein the oil phase and the non-ionic surfactant are in a ratio of 1 to 5:2 to 5 by weight percentage to acquire the homogeneous milky emulsion system.

14. The composition according to claim 11, wherein the oil phase and deionized water are in a ratio of 1 to 5:4 to 7 by weight percentage to acquire the homogeneous milky emulsion system.

15. The composition according to claim 11, wherein the non-ionic surfactant is sorbitan monooleate, sorbitan monolaurate, polyoxyethylene (20) sorbitan trioleate, or polyoxyethylene (20) sorbitan monooleate.

16. The composition according to claim 11, wherein the long chain alkyl esters of illipe fat are acquired through alcoholysis of illipe fat by a long chain alcohol in a ratio of 1:1 to 4 in the presence of lipase in an organic solvent, wherein the long chain alcohol has a carbon chain of 12 to 18 carbon atoms per molecule.

17. The composition according to claim 16, wherein the organic solvent has a log P value more than 3.5.

18. The composition according to claim 16, wherein the lipase is acquired from *Rhizomucor miehei*.

19. A composition for preparing cosmetic or pharmaceutical products, comprising:
a two or three phase isotropic emulsion system comprising:
an oil phase including long chain alkyl esters of illipe fat and a solubilizer, wherein the long chain alkyl has a carbon chain of 12-18 carbon atoms per molecular;
a non-ionic surfactant; and
deionized water;
wherein the solubilizer is a mixture of polyethyleneglycol-40 hydrogenated castor oil, polysorbate 20 and octoxynol-12.

20. The composition according to claim 19, wherein the long chain alkyl esters derived from illipe fat and the solubilizer are in a ratio of 4 to 2:2 to 1 by weight percentage.

21. The composition according to claim 19, wherein the oil phase and the non-ionic surfactant are in a ratio of 3 to 5:3 to 7 by weight percentage to acquire the isotropic emulsion system.

22. The composition according to claim 19, wherein the oil phase and deionized water are in a ratio of 3 to 5:1 to 4 by weight percentage to acquire the isotropic emulsion system.

23. The composition according to claim 19, wherein the non-ionic surfactant is sorbitan monooleate, sorbitan monolaurate, polyoxyethylene (20) sorbitan trioleate, or polyoxyethylene (20) sorbitan monooleate.

24. The composition according to claim 19, wherein the long chain alkyl esters of illipe fat are acquired through alcoholysis of illipe fat by a long chain alcohol in a ratio of 1:1 to 4 in the presence of lipase in an organic solvent, wherein the long chain alcohol has a carbon chain of 12 to 18 carbon atoms per molecule.

25. The composition according to claim 24, wherein the organic solvent has a log P value more than 3.5.

26. The composition according to claim 24, wherein the lipase is acquired from *Rhizomucor miehei*.

\* \* \* \* \*